(12) United States Patent
Li (10) Patent No.: US 10,307,124 B2
(45) Date of Patent: Jun. 4, 2019

(54) IMAGE DISPLAY DEVICE, METHOD, AND PROGRAM FOR DETERMINING COMMON REGIONS IN IMAGES

(71) Applicant: FUJIFILM Corporation, Tokyo (JP)

(72) Inventor: Yuanzhong Li, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/046,264

(22) Filed: Jul. 26, 2018

(65) Prior Publication Data

US 2018/0325478 A1 Nov. 15, 2018

Related U.S. Application Data

(63) Continuation of application No. PCT/JP2017/007502, filed on Feb. 27, 2017.

(30) Foreign Application Priority Data

Mar. 9, 2016 (JP) .................................. 2016-045137

(51) Int. Cl.
*A61B 6/00* (2006.01)
*G06K 9/32* (2006.01)
(Continued)

(52) U.S. Cl.
CPC ............ *A61B 6/463* (2013.01); *G06K 9/3233* (2013.01); *G06K 9/38* (2013.01); *G06K 9/46* (2013.01);
(Continued)

(58) Field of Classification Search
CPC ......... A61B 6/463; A61B 6/503; A61B 6/505; G06T 3/40; G06T 7/55;
(Continued)

(56) References Cited

U.S. PATENT DOCUMENTS

2014/0212014 A1* 7/2014 Kim ..................... G06T 3/0068
382/131
2015/0297157 A1 10/2015 Mukumoto
(Continued)

FOREIGN PATENT DOCUMENTS

| JP | 62-44224 A | 2/1987 |
| JP | 8-294485 A | 11/1996 |

(Continued)

OTHER PUBLICATIONS

International Preliminary Report on Patentability and Written Opinion of the International Searching Authority(Forms PCT/IB/326, PCT/IB/373 and PCT/ISA/237), dated Sep. 20, 2018, for International Application No. PCT/JP2017/007502, with an English Translation of the Written Opinion.
International Search Report (Form PCT/ISA/210), dated Jun. 6, 2017, for International Application No. PCT/JP2017/007502, with an English translation.
(Continued)

*Primary Examiner* — Jacinta M Crawford
(74) *Attorney, Agent, or Firm* — Birch, Stewart, Kolasch & Birch, LLP (57) ABSTRACT

An image acquisition unit acquires a plurality of medical images, and a common region determination unit determines common regions commonly present in the plurality of medical images. An enlargement ratio determination unit determines an enlargement ratio, which is for displaying the plurality of common regions in the plurality of medical images with the same size, for each of the plurality of medical images. A display control unit applies the determined enlargement ratio to the plurality of common regions, and displays images of the plurality of common regions after applying the enlargement ratio on a display.

9 Claims, 8 Drawing Sheets

(51) Int. Cl.
*G06K 9/46* (2006.01)
*G06T 3/40* (2006.01)
*G06K 9/62* (2006.01)
*G06K 9/38* (2006.01)
*G06T 7/55* (2017.01)

(52) U.S. Cl.
CPC .......... *G06K 9/6202* (2013.01); *G06K 9/6211* (2013.01); *G06T 3/40* (2013.01); *G06T 7/55* (2017.01); *A61B 6/503* (2013.01); *A61B 6/505* (2013.01); *G06K 2009/6213* (2013.01); *G06K 2209/05* (2013.01); *G06T 2207/10081* (2013.01); *G06T 2207/30012* (2013.01); *G06T 2207/30048* (2013.01); *G06T 2207/30061* (2013.01)

(58) Field of Classification Search
CPC . G06T 2207/10081; G06T 2207/30012; G06T 2207/30048; G06T 2207/30061; G06K 9/3233; G06K 9/38; G06K 9/46; G06K 9/6202; G06K 9/6211; G06K 2009/6213; G06K 2209/05
USPC ........................................ 382/128, 131, 132
See application file for complete search history.

(56) References Cited

U.S. PATENT DOCUMENTS

| | | | |
|---|---|---|---|
| 2015/0347464 A1* | 12/2015 | Takata | ................ H01L 29/7835 707/728 |
| 2015/0356245 A1 | 12/2015 | Kozuka et al. | |
| 2015/0379374 A1* | 12/2015 | Fukuda | ................. G06T 7/0016 382/132 |

FOREIGN PATENT DOCUMENTS

| | | |
|---|---|---|
| JP | 2002-253540 A | 9/2002 |
| JP | 2003-10172 A | 1/2003 |
| JP | 2003-265416 A | 9/2003 |
| JP | 2008-188177 A | 8/2008 |
| JP | 2012-35124 A | 2/2012 |
| JP | 2013-202051 A | 10/2013 |
| JP | 2015-171437 A | 10/2015 |
| JP | 2015-213749 A | 12/2015 |
| JP | 2016-12346 A | 1/2016 |

OTHER PUBLICATIONS

Japanese Office Action dated Jan. 8, 2019, for Japanese Patent Application No. 2016-045137, with an English machine translation.

* cited by examiner

IMAGE DISPLAY DEVICE, METHOD, AND PROGRAM FOR DETERMINING COMMON REGIONS IN IMAGES

CROSS REFERENCE TO RELATED APPLICATIONS

The present application is a Continuation of PCT International Application No. PCT/JP2017/007502 filed on Feb. 27, 2017, which claims priority under 35 U.S.C. § 119(a) to Japanese Patent Application No. 2016-045137 filed on Mar. 9, 2016. Each of the above applications is hereby expressly incorporated by reference, in its entirety, into the present application.

BACKGROUND

Technical Field

The present invention relates to an image display device, method, and program for displaying a plurality of images for comparison.

Background Art

In recent years, in the field of medical images, in addition to X-ray imaging apparatuses, modalities using various techniques, such as an X-ray computed tomography (CT) apparatus, an ultrasound (US) diagnostic apparatus, a magnetic resonance imaging (MRI) apparatus, a positron emission tomography (PET) apparatus, and a single-photon emission tomography (SPET) apparatus, are used. With an increase in the speed of such modalities and an improvement in performance, such as multi-slice correspondence, it is possible to acquire hundreds to thousands of high-resolution tomographic images by imaging a plurality of parts of a subject in one imaging series.

Comparative interpretation, in which a plurality of medical images are displayed on a display device such as a liquid crystal display and image interpretation is performed while comparing the images, has been performed in the related art. For example, by displaying the current and past medical images of the subject for comparative interpretation, it is possible to check the degree of progress of a lesion or to detect the abnormality at an early stage. In order to facilitate such comparative interpretation, a technique for displaying a medical image on the display device has been proposed. For example, JP2003-265416A has proposed a method of setting an enlargement ratio, at which the sizes of common imaged parts become equal, for two medical images for comparative interpretation and displaying the two medical images by enlarging and reducing the two medical images according to the set enlargement ratio. A method of displaying a plurality of CT images for comparison by making the sizes of the CT images equal based on the pixel size (refer to JP1996-294485A (JP-H08-294485A)) and a method in which enlargement of one of the two medical images for comparison causes enlargement of the other medical image (refer to JP2012-35124A and JP2015-171437A) have also been proposed.

In the case of acquiring medical images for performing the comparative interpretation described above, the subject is imaged so as to include a part to be subjected to the comparative interpretation. However, it is difficult to perform imaging so that the imaging ranges are completely the same all the time. For example, in the case of performing comparative interpretation using a CT image of an axial cross section having a cervical spine as a subject, the cervical spine is not always located at the center of the image, and the cervical spine may be included at a position shifted from the center of the image. Depending on the imaging conditions, the size of the region of the cervical spine included in the image may be different among images. In addition, depending on the posture at the time of imaging, the shoulder of the subject may be included or may not be included in the CT image. Thus, in the case of performing the comparative interpretation using medical images having different imaging ranges or medical images in which a part other than a target part is included or not included, even in a case where the size of the target part is made to be the same as in JP2003-265416A, the position of the target part is different among a plurality of medical images or an unnecessary part is included or not included. For this reason, it is difficult to perform the comparative interpretation efficiently.

In this case, it is conceivable to manually extract only common parts from a plurality of medical images while observing the plurality of medical images and match the sizes of the extracted parts with each other. However, such an operation is very troublesome, and the burden on the user is heavy.

SUMMARY

The present invention has been made in view of the above circumstances, and it is an object of the present invention to make it possible to effectively view a plurality of medical images to be subjected to comparative interpretation.

An image display device according to the present invention comprises: image acquisition unit for acquiring a plurality of medical images; common region determination unit for determining common regions commonly present in the plurality of medical images; enlargement ratio determination unit for determining an enlargement ratio, which is for displaying the plurality of common regions in the plurality of medical images with the same size, for each of the plurality of medical images; and display control unit for applying the determined enlargement ratio to the plurality of common regions and displaying images of the plurality of common regions after applying the enlargement ratio on display unit.

For the enlargement ratio determined for a plurality of medical images, in a case where the enlargement ratio of one medical image is 1, the common regions of all the medical images have the same size by enlarging or reducing the common regions of the other medical images with the determined enlargement ratio even without enlarging or reducing the one medical image. "Applying the enlargement ratio" includes not enlarging or reducing the common region of the medical image as in a case where the enlargement ratio is 1.

In the image display device according to the present invention, the common region determination unit may determine the common regions by extracting feature points from the plurality of medical images and performing matching using the feature points among the plurality of medical images.

In the image display device according to the present invention, the common region determination unit may extract anatomical regions common to the plurality of medical images from the plurality of medical images and determine the common regions based on the extracted anatomical regions.

The "anatomical region" means a partial region of the human body, such as an outline representing the specific organ, specific bone, and skin surface of the subject included in the medical image.

In the image display device according to the present invention, in a case where a plurality of anatomical regions are present in each of the plurality of medical images, the common region determination unit may extract one anatomical region from each of the plurality of medical images, determine other anatomical regions in other medical images other than one medical image of the plurality of medical images based on a positional relationship between the one anatomical region extracted in the one medical image and the other anatomical regions other than the one anatomical region, and determine the common regions based on the one anatomical region and the other anatomical regions extracted in the plurality of medical images.

In the image display device according to the present invention, the common region determination unit may determine the common regions by extracting at least a partial region of a subject region from each of the plurality of medical images and performing registration of at least the partial region of the subject region among the plurality of medical images.

In the image display device according to the present invention, the common region determination unit may perform the registration by binarizing each of the plurality of medical images.

The "subject region" is a region where the subject that is an imaging target in the medical image is present.

In the image display device according to the present invention, the common region determination unit may determine the common regions by matching actual sizes of the plurality of medical images with each other.

In this case, the common region determination unit may match the actual sizes with each other based on information of a distance between centers of adjacent pixels, which is given to each of the plurality of medical images.

"Matching the actual sizes with each other" means enlarging or reducing medical images so that the line segments having the same length (the same number of pixels) actually have the same length in each of the plurality of medical images. Specifically, the actual sizes may be matched with each other based on the distance between the centers of adjacent pixels.

In the image display device according to the present invention, the display control unit may display images of rectangular regions including the common regions on the display unit.

"Images of rectangular regions including the common regions" means images of rectangular regions including common regions therein. It is not necessary to completely include the common region inside, and an image not including a part of the common region within a range not affecting the observation may be applied. As long as the common region is included inside, an image circumscribing the common region may be applied, or an image in which a rectangular region circumscribing the common region is enlarged or reduced with a predetermined margin may be applied.

In the image display device according to the present invention, the display control unit may display images of the plurality of common regions after applying the enlargement ratio side by side.

In the image display device according to the present invention, the display control unit may perform switching display among images of the plurality of common regions after applying the enlargement ratio.

The switching display may be switching a plurality of common regions according to an instruction from the outside or may be switching images of a plurality of common regions at fixed time intervals.

The image display device according to the present invention may further comprise image processing unit for performing image processing for matching image qualities for images of the plurality of common regions.

An image display method according to the present invention comprises: acquiring a plurality of medical images; determining common regions commonly present in the plurality of medical images; determining an enlargement ratio, which is for displaying the plurality of common regions in the plurality of medical images with the same size, for each of the plurality of medical images; and applying the determined enlargement ratio to the plurality of common regions and displaying images of the plurality of common regions after applying the enlargement ratio on display unit.

In addition, a program causing a computer to execute the image display method according to the present invention may be provided.

According to the present invention, common regions commonly present in the plurality of medical images are determined, an enlargement ratio for displaying the plurality of common regions in the plurality of medical images with the same size is determined for each of the plurality of medical images, the determined enlargement ratio is applied to the plurality of common regions, and the plurality of common regions after applying the enlargement ratio is displayed on the display unit. For this reason, even in a case where the user does not perform any processing, common regions having the same size in a plurality of medical images are displayed on the display unit. Therefore, it is possible to effectively view a plurality of medical images to be subjected to comparative interpretation.

DESCRIPTION OF THE EMBODIMENTS

Figure 1:
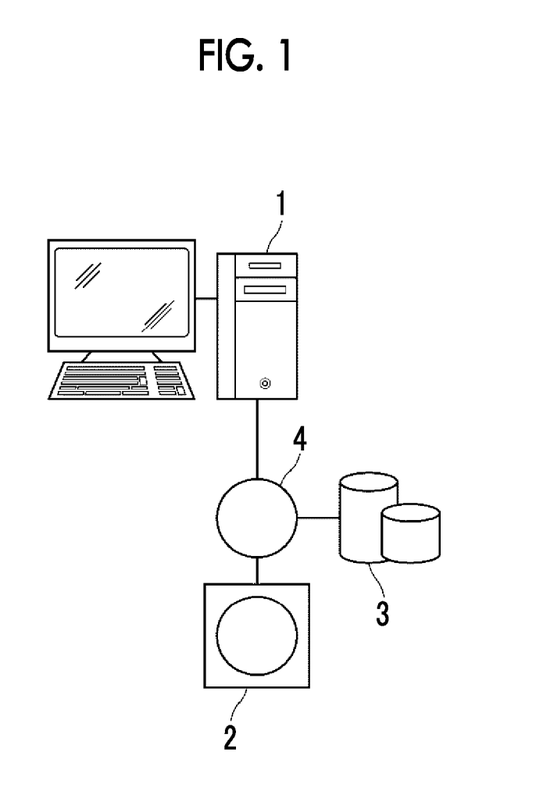
FIG. 1 is a hardware configuration diagram showing an outline of a diagnostic support system to which an image display device according to a first embodiment of the present invention is applied.

Hereinafter, embodiments of the present invention will be described with reference to the diagrams. FIG. 1 is a hardware configuration diagram showing the outline of a diagnostic support system to which an image display device according to a first embodiment of the present invention is applied. As shown in FIG. 1, in the diagnostic support system, an image display device 1 according to the present embodiment, a three-dimensional image capturing apparatus 2, and an image storage server 3 are communicably connected to each other through a network 4. In the diagnostic support system, for comparative diagnosis of a part to be examined of the subject, a current three-dimensional image and a past three-dimensional image are displayed on the image display device 1.

The three-dimensional image capturing apparatus 2 is an apparatus that generates a three-dimensional image showing a part, which is a part to be examined of the subject, by imaging the part. Specifically, the three-dimensional image capturing apparatus 2 is a CT apparatus, an MRI apparatus, a PET apparatus, or the like. A three-dimensional image V0 generated by the three-dimensional image capturing apparatus 2 is transmitted and stored in the image storage server 3. In the present embodiment, it is assumed that the diagnostic target part of the subject is the cervical spine, the three-dimensional image capturing apparatus 2 is a CT apparatus, and a three-dimensional image formed by tomographic images of a plurality of axial cross sections of the cervical spine of the subject is generated.

The image storage server 3 is a computer that stores and manages various kinds of data, and includes a large-capacity external storage device and software for database management. The image storage server 3 communicates with other devices through the wired or wireless network 4 to transmit and receive image data or the like. Specifically, the image storage server 3 acquires image data, such as a three-dimensional image generated by the three-dimensional image capturing apparatus 2, through the network, and stores the image data in a recording medium, such as a large-capacity external storage device, to manage the image data. The storage format of image data and the communication between devices through the network 4 is based on a protocol, such as a digital imaging and communication in medicine (DICOM). In the present embodiment, it is assumed that three-dimensional images of the cervical spine with different imaging timings for the same subject are stored in the image storage server 3.

The image display device 1 is realized by installing an image display program of the present invention on one computer. The computer may be a workstation or a personal computer that is directly operated by a doctor who performs diagnosis, or may be a server computer connected to these through a network. The image display program is distributed by being recorded on a recording medium, such as a digital versatile disc (DVD) or a compact disk read only memory (CD-ROM), and is installed onto the computer from the recording medium. Alternatively, the image display program is stored in a storage device of a server computer connected to the network or in a network storage so as to be accessible from the outside, and is downloaded and installed onto a computer used by a doctor as necessary.

Figure 2:
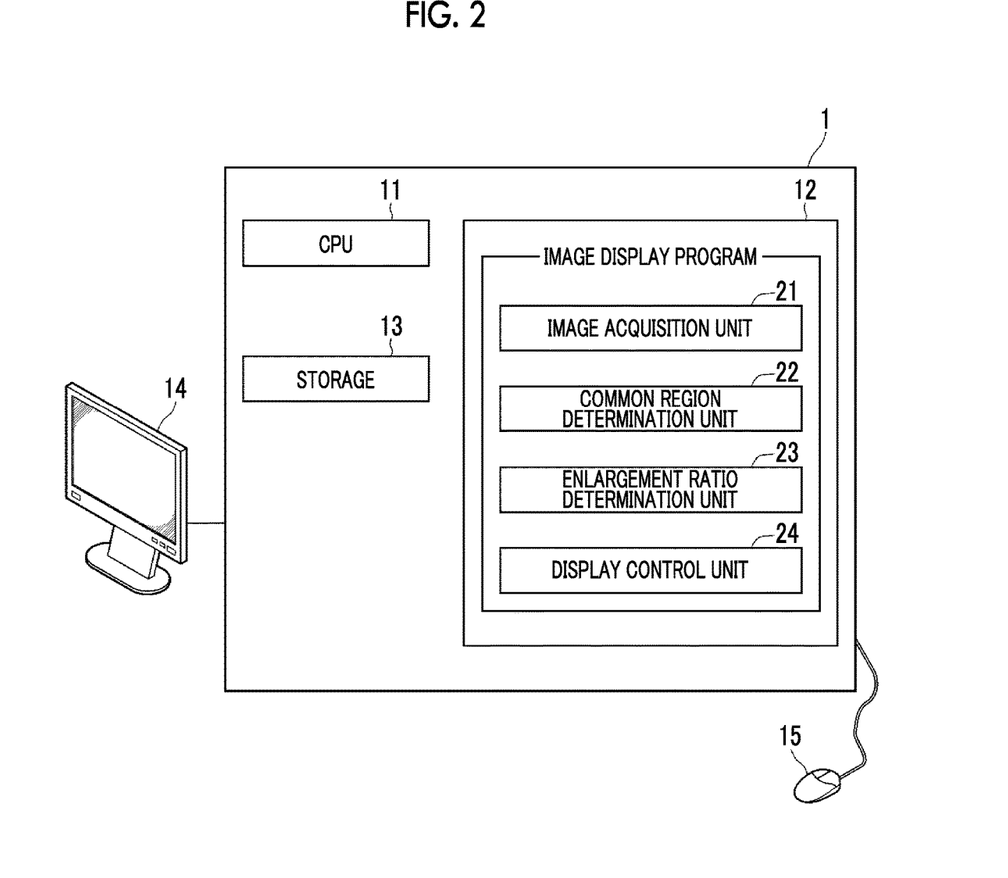
FIG. 2 is a schematic block diagram showing the configuration of the image display device according to the first embodiment.

FIG. 2 is a diagram showing the schematic configuration of an image display device realized by installing an image display program on a computer. As shown in FIG. 2, the image display device 1 includes a central processing unit (CPU) 11, a memory 12, and a storage 13 as the configuration of a standard workstation. A display 14 and an input unit 15, such as a mouse, are connected to the image display device 1. The display 14 corresponds to display unit.

Current and past three-dimensional images of the subject acquired from the image storage server 3 through the network 4 and various kinds of information including information necessary for processing are stored in the storage 13. In the present embodiment, it is assumed that, for the same subject, a latest three-dimensional image (hereinafter, referred to as a current three-dimensional image V1) and three-dimensional images V2 and V3 with different imaging times acquired in the past are stored. In addition, it is assumed that three-dimensional images are collectively referred to as the three-dimensional image V0 in some cases.

An image display program is stored in the memory 12. As processing to be executed by the CPU 11, the image display program defines: image acquisition processing for acquiring tomographic images T1 to T3 of corresponding axial tomographic planes to be examined in the three-dimensional images V1 to V3 including the cervical spine that is a diagnostic target in comparative interpretation, the three-dimensional images V1 to V3 being acquired by the three-dimensional image capturing apparatus 2; common region determination processing for determining common regions that are commonly present in the tomographic images T1 to T3; enlargement ratio determination processing for determining an enlargement ratio, which is for displaying a plurality of common regions in the tomographic images T1 to T3 with the same size, for each of the tomographic images T1 to T3; and display control processing for applying the enlargement ratio determined for the plurality of common regions and displaying the images of the plurality of common regions after applying the enlargement ratio on the display 14.

The CPU 11 executes these processes according to the program, so that the computer functions as an image acquisition unit 21, a common region determination unit 22, an enlargement ratio determination unit 23, and a display control unit 24. The image display device 1 may include a plurality of processors for performing image acquisition processing, common region determination processing, enlargement ratio determination processing, and display control processing. The tomographic images T1 to T3 correspond to medical images.

The image acquisition unit 21 acquires tomographic images T1 to T3 of the corresponding axial tomographic planes, which are to be examined, in the three-dimensional images V1 to V3 from the image storage server 3. The image acquisition unit 21 may acquire the three-dimensional images V1 to V3 from the image storage server 3 and acquire the tomographic images T1 to T3 from the three-dimensional images V1 to V3. In a case where the three-dimensional images V1 to V3 are already stored in the storage 13, the tomographic images T1 to T3 may be acquired from the storage 13.

The common region determination unit 22 determines common regions that are commonly present in the tomographic images T1 to T3. In the present embodiment, the common region determination unit 22 determines a common region by extracting feature points from each of the tomographic images T1 to T3 and performing matching among the extracted feature points. First, extraction and matching of feature points will be described.

Any known method can be used for extraction and matching of feature points. For example, it is possible to use a template matching method in which a feature point and a region of, for example, 9×9 pixels centered on the feature point in a tomographic image are extracted as a template and corresponding feature points among tomographic images are searched for using the extracted template. In addition, a method may be used in which feature points included in the tomographic images T1 to T3, such as edges, intersections of edges, and corners of edges, are detected using an algorithm, such as scale-invariant feature transform (SIFT) or speeded up robust features (SURF), and the detected feature points are matched with each other.

Here, the SIFT is a method of describing feature amounts, which are invariant with respect to the rotation and scale change of an image, at feature points and performing registration of a plurality of images based on the described feature amounts. The SURF is a method of performing registration at a higher speed by replacing processing performed in the SIFT with approximate processing.

It is possible to use a method for detecting feature points invariant with respect to scale change described in "Distinctive Image Features from Scale-Invariant Keypoints, David G. Lowe, International Journal of Computer Vision, 2004" (reference 1). In addition, it is possible to use a method that makes the methods of SIFT and SURF faster, which is described in "ORB: an efficient alternative to SIFT or SURF. Proc. IEEE International Conference on Computer Vision, pp. 2564-2571, 2011" (reference 2).

Figure 3:
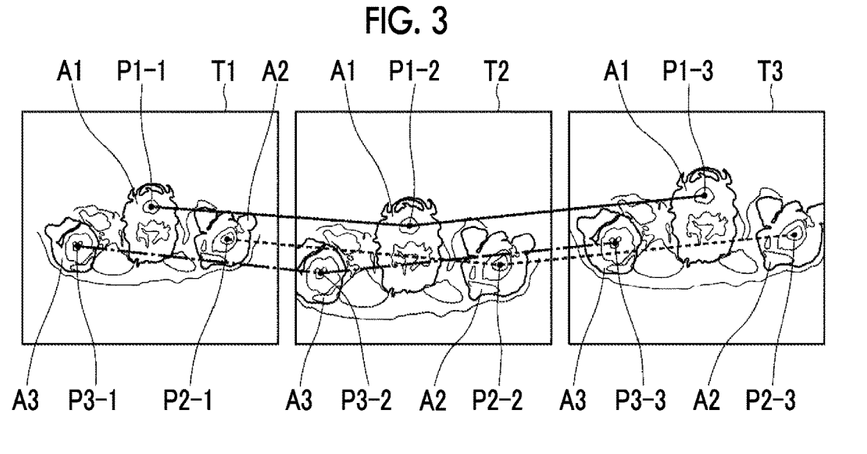
FIG. 3 is a diagram showing the results of detection and matching of feature points.

FIG. 3 is a diagram showing the results of detection and matching of feature points. As shown in FIG. 3, each of the three tomographic images T1 to T3 includes a cervical spine region A1 and shoulder regions A2 and A3. However, in the tomographic images T1 to T3, the positions and sizes of the cervical spine region A1 and the shoulder regions A2 and A3 are different.

The common region determination unit 22 detects a feature point P1-1 in the cervical spine region A1, a feature point P2-1 in the shoulder regions A2, and a feature point P3-1 in the shoulder regions A3, in the tomographic image T1, and performs feature point matching among the tomographic images T1 to T3. As a result, in the tomographic images T1 to T3, the feature points P1-1, P1-2, and P1-3 in the cervical spine region A1, the feature points P2-1, P2-2, and P2-3 in the shoulder region A2, and the feature points P3-1, P3-2, and P3-3 in the shoulder region A3 are matched with each other. In FIG. 3, the solid line indicates that the feature points P1-1, P1-2, and P1-3 are matched with each other, the broken line indicates that the feature points P2-1, P2-2, and P2-3 are matched with each other, and the one-dot chain line indicates that the feature points P3-1, P3-2, and P3-3 are matched with each other. In FIG. 3, only three feature points are detected in each of the tomographic images T1 to T3. In practice, however, a number of feature points are detected and matched.

The common region determination unit 22 determines upper, lower, left, and right edge portions closest to the feature points matched among the tomographic images T1 to T3 based on the result of matching among the feature points.

Figure 4:
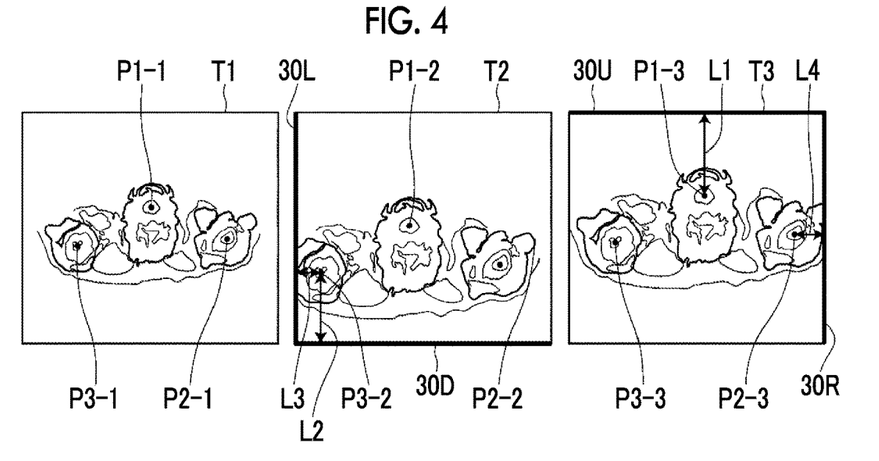
FIG. 4 is a diagram illustrating the determination of closest edge portions in the first embodiment.

Hereinafter, the upper, lower, left, and right edge portions closest to the feature points matched among the tomographic images T1 to T3 are referred to as a closest upper edge portion, a closest lower edge portion, a closest left edge portion, and a closest right edge portion. FIG. 4 is a diagram illustrating the determination of closest edge portions. First, in order to determine closest upper edge portions, the common region determination unit 22 calculates the distances between all the feature points and the upper edge portion in each of the tomographic images T1 to T3. Then, an upper edge portion of a tomographic image including a feature point for which the calculated distance is the smallest is determined as the closest upper edge portion. In the present embodiment, as shown in FIG. 4, since the distance between the feature point P1-3 in the tomographic image T3 and the upper edge portion of the tomographic image T3 is the smallest, the common region determination unit 22 determines the upper edge portion of the tomographic image T3 as a closest upper edge portion 30U.

Next, in order to determine the closest lower edge portion, the common region determination unit 22 calculates the distances between all the feature points and the lower edge portion in each of the tomographic images T1 to T3. Then, a lower edge portion of a tomographic image including a feature point for which the calculated distance is the smallest is determined as the closest lower edge portion. In the present embodiment, as shown in FIG. 4, since the distance between the feature point P3-2 in the tomographic image T2 and the lower edge portion of the tomographic image T2 is the smallest, the common region determination unit 22 determines the lower edge portion of the tomographic image T2 as a closest lower edge portion 30D.

Similarly, the common region determination unit 22 determines a closest left edge portion and a closest right edge portion. In the present embodiment, since the distance between the feature point P3-2 in the tomographic image T2 and the left edge portion of the tomographic image T2 is the smallest, the common region determination unit 22 determines the left edge portion of the tomographic image T2 as a closest left edge portion 30L. In addition, since the distance between the feature point P2-3 in the tomographic image T3 and the right edge portion of the tomographic image T3 is the smallest, the common region determination unit 22 determines the right edge portion of the tomographic image T3 as a closest right edge portion 30R. In FIG. 4, the determined upper, lower, left, and right closest edge portions are shown by bold lines.

The common region determination unit 22 determines common regions in the tomographic images T1 to T3 based on the determined upper, lower, left, and right closest edge portions. In the present embodiment, it is assumed that each common region is rectangular. First, determination of an upper edge portion of a common region will be described. In the present embodiment, since the upper edge portion of the tomographic image T3 is determined as the closest upper edge portion 30U, the common region determination unit 22 calculates a distance L1 from the feature point P1-3 to the closest upper edge portion 30U in the tomographic image T3, and sets temporary upper edge portions at positions, which are away from the feature points P1-1 and P1-2 by the distance L1, for the tomographic images T1 and T2. In this case, since the size of a region (hereinafter, referred to as a subject region) of the subject, which is an imaging target included in each of the tomographic images T1 to T3, is different in each of the tomographic images T1 to T3, a temporary upper edge portion is set by normalizing the distance L1. For example, a ratio of the distance between the feature point P1-1 and the feature point P3-1 in the tomographic image T1 to the distance between the feature point P1-3 and the feature point P3-3 in the tomographic image T3 is calculated and the calculated ratio is multiplied by the distance L1, and then a temporary upper edge portion is set for the tomographic image T1. Similarly, a ratio of the distance between the feature point P1-2 and the feature point P3-2 in the tomographic image T2 to the distance between the feature point P1-3 and the feature point P3-3 in the tomographic image T3 is calculated and the calculated ratio is multiplied by the distance L1, and then a temporary upper edge portion is set for the tomographic image T2.

Regarding the lower edge portion of the common region, in the present embodiment, the lower edge portion of the tomographic image T2 is determined as the closest lower edge portion 30D. Therefore, the common region determination unit 22 calculates a distance L2 from the feature point P3-2 to the closest lower edge portion 30D in the tomographic image T2, and sets temporary lower edge portions at positions, which are away from the feature points P3-1 and P3-2 by the distance L2, for the tomographic images T2 and T3. In this case, since the size of the subject region included in each of the tomographic images T1 to T3 is different, a temporary lower edge portion is set by normalizing the distance L2 in the same manner as in the case of setting the temporary upper edge portion.

Regarding the left edge portion of the common region, in the present embodiment, the left edge portion of the tomographic image T2 is determined as the closest left edge portion 30L. Therefore, the common region determination unit 22 calculates a distance L3 from the feature point P3-2 to the closest left edge portion 30L in the tomographic image T2, and sets temporary left edge portions at positions, which are away from the feature points P3-1 and P3-2 by the distance L3, for the tomographic images T2 and T3. In this case, a temporary left edge portion is set by normalizing the distance L3 in the same manner as in the case of setting the temporary upper edge portion.

Figure 5:
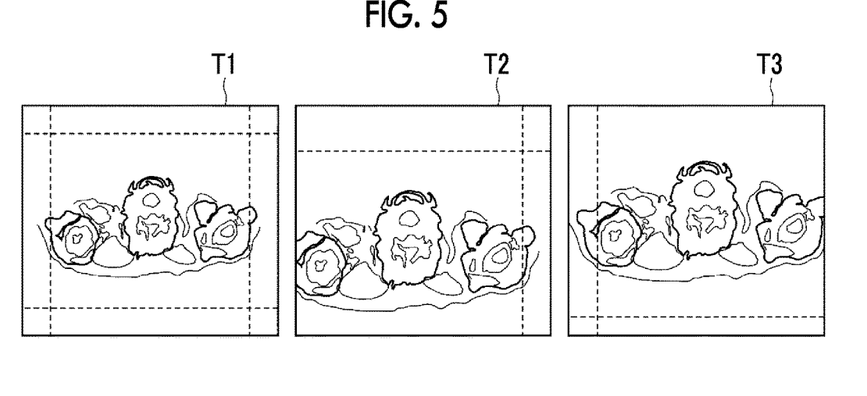
FIG. 5 is a diagram showing temporary upper, lower, left, and right edge portions set in a tomographic image.

Regarding the right edge portion of the common region, in the present embodiment, the right edge portion of the tomographic image T3 is determined as the closest right edge portion 30R. Therefore, the common region determination unit 22 calculates a distance L4 from the feature point P2-3 to the closest right edge portion 30R in the tomographic image T3, and sets temporary right edge portions at positions, which are away from the feature points P2-1 and P2-2 by the distance L4, for the tomographic images T1 and T2. In this case, a temporary right edge portion is set by normalizing the distance L4 in the same manner as in the case of setting the temporary upper edge portion. The temporary upper, lower, left, and right edge portions set in the tomographic images T1 to T3 are shown by broken lines in FIG. 5.

Figure 6:
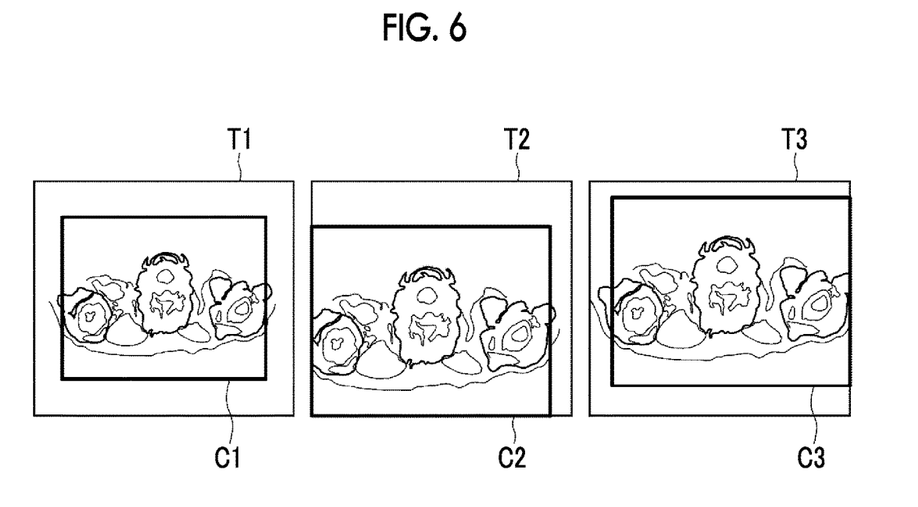
FIG. 6 is a diagram showing a common region determined in the first embodiment.

In a case where the temporary upper, lower, left, and right edge portions are determined, the common region determination unit 22 sets a frame of a region, which is defined by the upper, lower, left, and right edge portions and upper, lower, left, and right closest edge portions of each tomographic image, in each of the tomographic images T1 to T3. Then, a common region is determined by adjusting the positions of the temporary upper, lower, left, and right edge portions and the positions of the upper, lower, left, and right closest edge portions of each tomographic image so that the aspect ratio of the region surrounded by the frame is the same as that in the image to be displayed. FIG. 6 is a diagram showing determined common regions. As shown in FIG. 6, determined common regions C1 to C3 are shown in the tomographic images T1 to T3. In the common region C2 set in the tomographic image T2, the lower edge portion is located on the slightly upper side than the closest lower edge portion 30D. In the common region C3 set in the tomographic image T3, the upper edge portion is located on the slightly lower side than the closest upper edge portion 30U.

The enlargement ratio determination unit 23 determines enlargement ratios for displaying the common regions C1 to C3 with the same size for the respective tomographic images T1 to T3. In the present embodiment, enlargement ratios R1 to R3 for enlarging or reducing of the common regions C1 to C3 are determined for the respective tomographic images T1 to T3 so that the sizes of images to display the common regions C1 to C3 become equal. In addition, in a case where the size of the common region is the same as the size of the image to be displayed, the enlargement ratio for the common region is set to 1. Accordingly, the common region is substantially neither enlarged nor reduced.

Figure 7:
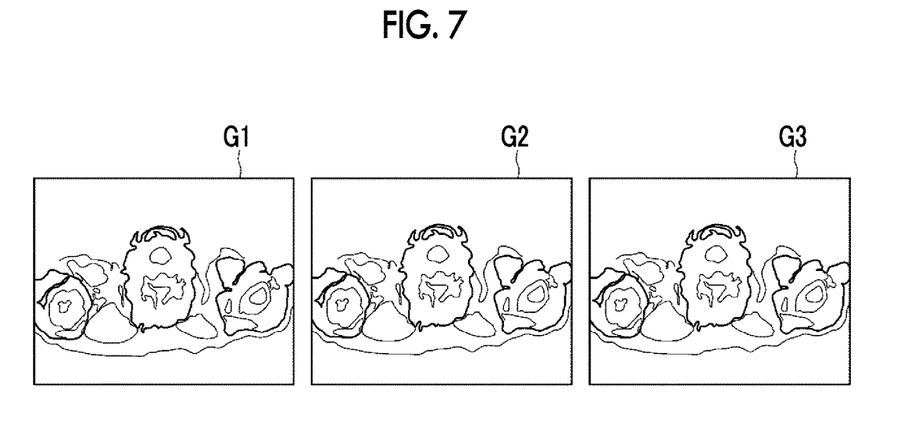
FIG. 7 is a diagram showing an image of a common region displayed on a display in the first embodiment.

The display control unit 24 applies the determined enlargement ratios R1 to R3 to the common regions C1 to C3, respectively, and displays the images of the common regions C1 to C3 after applying the enlargement ratios on the display 14. That is, the common regions C1 to C3 are enlarged or reduced according to the enlargement ratios R1 to R3, respectively, and images G1 to G3 of the enlarged or reduced common regions are displayed on the display 14. FIG. 7 is a diagram showing the images G1 to G3 of the common regions displayed on the display 14. As shown in FIG. 7, the images G1 to G3 of the common regions having the same size are displayed side by side. In the displayed images G1 to G3 of the common regions, the cervical spine region A1 and the shoulder regions A2 and A3 are included in approximately the same position with approximately the same size.

In the case of displaying the images G1 to G3 of the common regions, in consideration of the arrangement of the subject region in the common regions C1 to C3, a position where the subject region is interrupted by the frame, and the like, the images G1 to G3 of the common regions may be displayed with a certain margin with respect to the positions of the frames of the common regions C1 to C3. Alternatively, by displaying the tomographic images T1 to T3 in which the common regions C1 to C3 are set before displaying the images G1 to G3 of the common regions and modifying the positions and sizes of the common regions C1 to C3 in response to an instruction for modification by the user, the images G1 to G3 of the common regions may be displayed.

Figure 8:
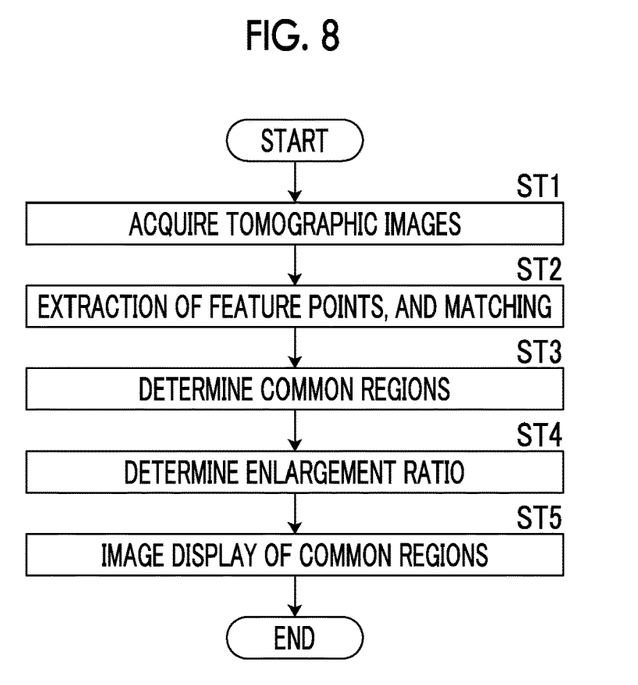
FIG. 8 is a flowchart showing the process performed in the first embodiment.

Next, the process performed in the first embodiment will be described. FIG. 8 is a flowchart showing the process performed in the first embodiment. First, the image acquisition unit 21 acquires the tomographic images T1 to T3 (step ST1), and the common region determination unit 22 extracts and matches feature points from the tomographic images T1 to T3 (step ST2) and determines the common regions C1 to C3, which are commonly present in the tomographic images T1 to T3, based on the results of extraction and matching of feature points (step ST3). Then, the enlargement ratio determination unit 23 determines enlargement ratios for displaying the common regions C1 to C3 with the same size for the respective tomographic images T1 to T3 (step ST4). Then, the display control unit 24 applies the determined enlargement ratios R1 to R3 to the common regions C1 to C3, respectively, displays the images G1 to G3 of the common regions C1 to C3 after applying the enlargement ratios on the display 14 (step ST5), and ends the process.

As described above, in the first embodiment, the common regions C1 to C3 that are commonly present in the plurality of tomographic images T1 to T3 are determined, the enlargement ratios R1 to R3 for displaying the common regions C1 to C3 with the same size are determined for the respective tomographic images T1 to T3, and the determined enlargement ratios R1 to R3 are applied to the plurality of common regions C1 to C3 to display the images G1 to G3 of the common regions. For this reason, even in a case where the user does not perform any processing, the images G1 to G3 of the common regions having the same size for the tomographic images T1 to T3 are displayed on the display 14. Therefore, it is possible to effectively view diagnostic target parts included in the plurality of tomographic images T1 to T3 to be subjected to comparative interpretation.

In the first embodiment, since each of the acquired tomographic images T1 to T3 is an image of one tomographic plane in each of the three-dimensional images V1 to V3, tomographic images of different tomographic planes are displayed by changing the positions of the tomographic planes of the displayed images G1 to G3. In this case, the tomographic images of different tomographic planes may be displayed by cutting out the same regions as the common regions, that is, regions having the same position and the same size as the common regions set in the tomographic images T1 to T3, and enlarging and reducing the regions to the size of the image to be displayed. For all the tomographic images included in the three-dimensional images V1 to V3, a common region may be determined among the tomographic images of the corresponding tomographic planes in the same manner as described above, and an image of the common region for the tomographic image of the tomographic plane switched in a case where the tomographic plane is switched may be displayed. In addition, an image of the common region may be displayed only for the tomographic image displayed first, and the tomographic image of the tomographic plane may be displayed as it is in a case where the tomographic plane is switched.

Next, a second embodiment of the present invention will be described. The configuration of an image display device according to the second embodiment is the same as the configuration of the image display device according to the first embodiment shown in FIG. 2, and only the processing performed by the common region determination unit 22 is different. Accordingly, the detailed description of the device will be omitted herein. The second embodiment is different from the first embodiment in that anatomical regions common between tomographic images included in a plurality of three-dimensional images are extracted from the tomographic images and common regions are determined based on the extracted anatomical regions.

Figure 9:
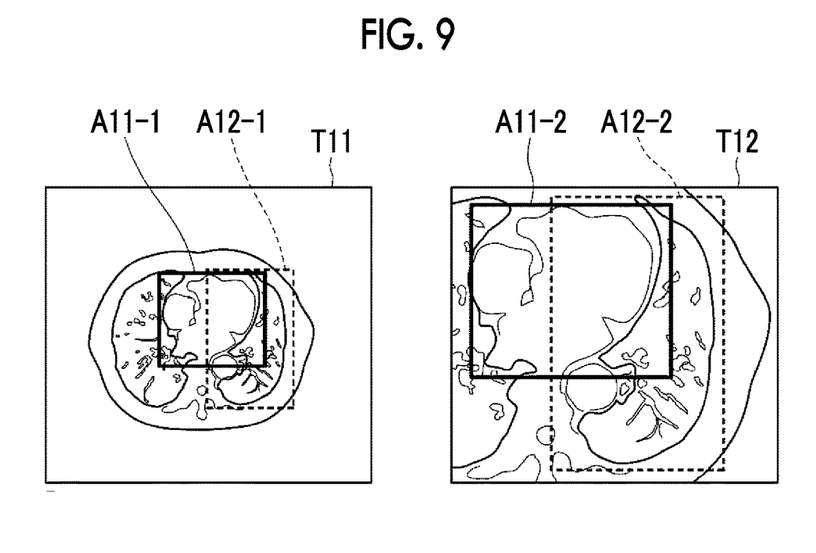
FIG. 9 is a diagram illustrating the extraction of an anatomical region from a tomographic image in a second embodiment.

Therefore, in the second embodiment, the common region determination unit 22 extracts an anatomical region from each tomographic image. FIG. 9 is a diagram illustrating the extraction of an anatomical region from each tomographic image in the second embodiment. In the second embodiment, it is assumed that tomographic images T11 and T12 of the axial cross section included in the three-dimensional image of the chest are used. The common region determination unit 22 extracts a heart region and a lung region as anatomical regions from the tomographic images T11 and T12.

As processing for extracting the heart, for example, as disclosed in JP2008-259682A, a method of performing cardiac recognition and extracting the heart based on the recognition result can be used. The method disclosed in JP2008-259682A is a method in which an input tomographic image is normalized, a number of feature amounts are calculated from the normalized tomographic image, the feature amounts calculated for each normalized tomographic image is input to a discriminator obtained by the AdaBoost method, a score for each part representing the part likelihood is calculated, and a part (that is, the heart) that is shown in the tomographic image so that the arrangement order of the body parts of the human body is maintained is determined using the dynamic programming method with the calculated part score as an input. It is also possible to use a method based on template matching (for example, refer to JP2002-253539A), a method using a unique image of each part (that is, the heart) (for example, refer to JP2003-10166A), and the like.

As processing for extracting the lung, it is possible to use any method, such as a method in which the signal value of each pixel in a tomographic image is expressed using a histogram and threshold processing is performed to extract the lung and a region growing method based on a seed point showing the lung. In the second embodiment, only the right lung is to be extracted.

It is also possible to extract the heart and the lung using the marginal space learning method described in "Marginal space learning for efficient detection of 2D/3D anatomical structures in medical images. Proc. Information Processing in Medical Imaging, 2009" (reference 3).

The common region determination unit 22 extracts rectangular regions including the heart and the lung, which are extracted in the tomographic images T11 and T12, as heart regions A11-1 and A11-2 and lung regions A12-1 and A12-2. In FIG. 9, the heart regions A11-1 and A11-2 are shown by the solid line, and the lung regions A12-1 and A12-2 are shown by the broken line. The heart regions A11-1 and A11-2 and the lung regions A12-1 and A12-2 correspond to anatomical regions.

Figure 10:
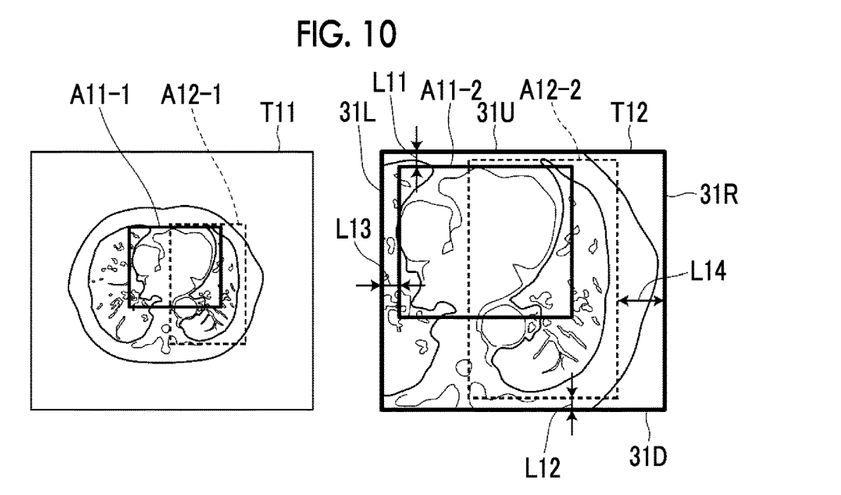
FIG. 10 is a diagram illustrating the determination of closest edge portions in the second embodiment.

Based on the extraction result of the heart region and the lung region, the common region determination unit 22 determines upper, lower, left, and right edge portions closest to the extracted heart region and lung region, that is, closest edge portions, in the tomographic images T11 and T12. In the second embodiment, distances from the heart region A11-2 and the lung region A12-2 in the tomographic image T12 to the upper edge portion, the lower edge portion, the left edge portion, and the right edge portion of the tomographic image T12 are shorter than distances from the heart region A11-1 and the lung region A12-1 in the tomographic image T11 to the upper edge portion, the lower edge portion, the left edge portion, and the right edge portion of the tomographic image T1. Therefore, as shown in FIG. 10, the common region determination unit 22 determines the upper edge portion, the lower edge portion, the left edge portion, and the right edge portion of the tomographic image T12 as a closest upper edge portion 31U, a closest lower edge portion 31D, a closest left edge portion 31L, and a closest right edge portion 31R, respectively.

The common region determination unit 22 determines common regions that are commonly present in the tomographic images T11 and T12 based on the determined upper, lower, left, and right closest edge portions. In the second embodiment, since the upper, lower, left, and right edge portions of the tomographic image T12 are determined as the closest upper edge portion 31U, the closest lower edge portion 31D, the closest left edge portion 31L, and the closest right edge portion 31R, the entire region of the tomographic image T12 becomes a common region C12. Accordingly, the common region determination unit 22 sets the frame of a common region C11 only for the tomographic image T11. Specifically, in the tomographic image T12, a distance L11 from the upper edge portion of the heart region A11-2 to the upper edge portion of the tomographic image T12 is calculated. Since the sizes of the heart region and the lung region are different between the tomographic images T11 and T12, the ratio of the sizes of the heart region A11-1 in the tomographic image T11 and the heart region A11-2 in the tomographic image T12 is calculated, the distance L11 is normalized by using the calculated ratio, and a temporary upper edge portion is set at a position away from the upper edge portion of the heart region A11-1 in the tomographic image T11 by the normalized distance L11.

For the lower edge portion of the common region, in the tomographic image T12, a distance L12 from the lower edge portion of the lung region A12-2 to the lower edge portion of the tomographic image T12 is calculated. In this case, as in the case of setting the temporary upper edge portion, the distance L12 is normalized, and a temporary lower edge portion is set at a position away from the lower edge portion of the lung region A12-1 in the tomographic image T11 by the normalized distance L12.

For the left edge portion of the common region, in the tomographic image T12, a distance L13 from the left edge portion of the heart region A11-2 to the left edge portion of the tomographic image T12 is calculated. In this case, as in the case of setting the temporary upper edge portion, the distance L13 is normalized, and a temporary left edge portion is set at a position away from the left edge portion of the heart region A11-1 in the tomographic image T11 by the normalized distance L13.

For the right edge portion of the common region, in the tomographic image T12, a distance L14 from the right edge portion of the lung region A12-2 to the right edge portion of the tomographic image T12 is calculated. In this case, as in the case of setting the temporary upper edge portion, the distance L14 is normalized, and a temporary right edge portion is set at a position away from the right edge portion of the lung region A12-1 in the tomographic image T11 by the normalized distance L14.

Figure 11:
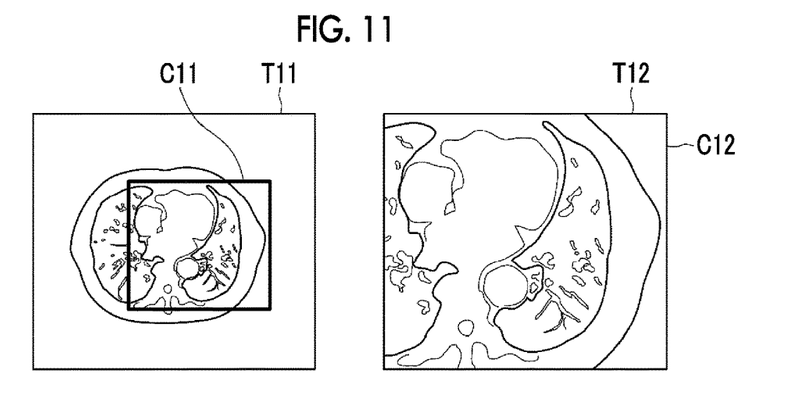
FIG. 11 is a diagram showing a common region determined in the second embodiment.

In a case where the temporary upper, lower, left, and right edge portions are determined, the common region determination unit 22 sets a frame of a region, which is defined by the upper, lower, left, and right edge portions and upper, lower, left, and right closest edge portions of each tomographic image, in each of the tomographic images T11 and T12. Then, a common region is determined by adjusting the positions of the temporary upper, lower, left, and right edge portions and the positions of the upper, lower, left, and right closest edge portions of each tomographic image so that the aspect ratio of the region surrounded by the frame is the same as that in the image to be displayed. FIG. 11 is a diagram showing determined common regions. As shown in FIG. 11, determined common regions C11 and C12 are shown in the tomographic images T11 and T12. In the tomographic image T12, the entire region is the common region C12.

Then, the enlargement ratio determination unit 23 determines enlargement ratios for displaying the common regions C11 and C12 with the same size for the respective tomographic images T11 and T12. The display control unit 24 applies the determined enlargement ratios to the common regions C11 and C12, and displays the images of the common regions C11 and C12 after applying the enlargement ratios on the display 14.

Figure 12:
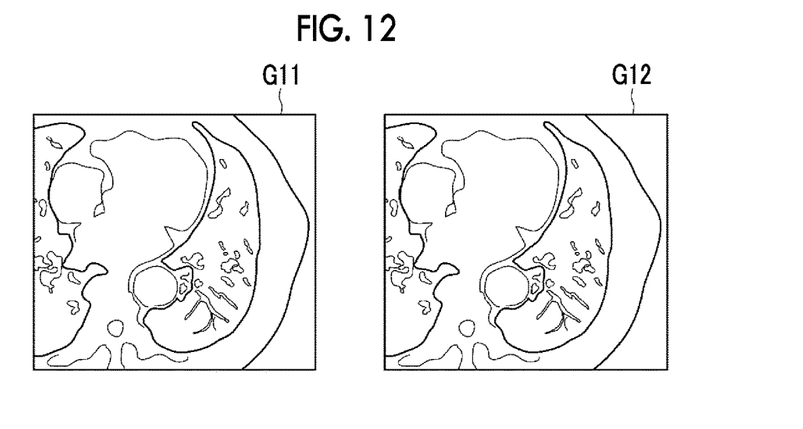
FIG. 12 is a diagram showing an image of a common region displayed on the display in the second embodiment.

FIG. 12 is a diagram showing an image of a common region displayed on the display 14 in the second embodiment. As shown in FIG. 12, images G11 and G12 of common regions are displayed side by side. In the displayed images G11 and G12 of the common regions, the heart region and the lung region are included in approximately the same position with approximately the same size.

Also in the second embodiment, as in the first embodiment, in the case of displaying the images G11 and G12 of the common regions, in consideration of the arrangement of the subject region in the common regions C11 and C12, a position where the subject region is interrupted by the frame, and the like, the images G11 and G12 of the common regions C11 and C12 may be displayed with a certain margin with respect to the position of each side of the frame. Alternatively, by displaying the tomographic images T11 and T12 in which the common regions C11 and C12 are set before displaying the images G11 and G12 of the common regions and modifying the positions and sizes of the common regions C11 and C12 in response to an instruction for modification by the user, the images G11 and G12 of the common regions may be displayed.

Figure 13:
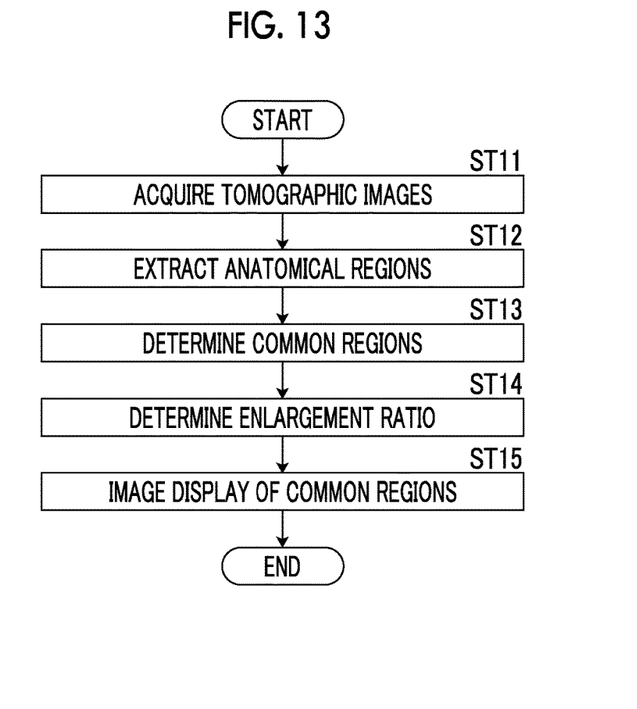
FIG. 13 is a flowchart showing the process performed in the second embodiment.

Next, the process performed in the second embodiment will be described. FIG. 13 is a flowchart showing the process performed in the second embodiment. First, the image acquisition unit 21 acquires the tomographic images T11 and T12 (step ST11). The common region determination unit 22 extracts an anatomical region from the tomographic images T11 and T12 (step ST12), and determines the common regions C11 and C12, which are commonly present in the tomographic images T11 and T12, based on the extraction result of the anatomical region (step ST13). Then, the enlargement ratio determination unit 23 determines enlargement ratios for displaying the common regions C11 and C12 with the same size for the respective tomographic images T11 and T12 (step ST14). Then, the display control unit 24 applies the determined enlargement ratios to the common regions C11 and C12, displays the images of the common regions C11 and C12 after applying the enlargement ratios on the display 14 (step ST15), and ends the process.

In the second embodiment described above, the heart region and the lung region are extracted from each of the tomographic images T11 and T12. However, only one of the heart region and the lung region, for example, only the heart region may be extracted. Hereinafter, this will be described as a third embodiment.

For the same subject, the positional relationship between the heart and the lung is almost constant irrespective of the imaging time of the three-dimensional image. For this reason, in each of the tomographic images T11 and T12, the anatomical positional relationship between the heart region and the lung region is known. Therefore, in a case where the position of the lung region with respect to the extracted heart region A11-1 in one tomographic image T11 is known, the position of the lung region can be seen from the position of the heart region A11-2 in the other tomographic image T12.

Therefore, in the third embodiment, the common region determination unit 22 extracts the heart region A11-1 and the lung region A12-1 only in the tomographic image T11, and specifies the position of the lung region with respect to the heart region A11-2 in the other tomographic image T12 based on the position of the lung region A12-1 with respect to the heart region A11-1 in the tomographic image T11. As a result, even in a case where the lung region is not extracted from the tomographic image T12, the position of the lung region in the tomographic image T12 can be determined from the positional relationship between the heart region A11-1 and the lung region A12-1 in the tomographic image T11. Accordingly, the common regions C11 and C12 can be determined from the heart region and the lung region in the tomographic images T11 and T12 in the same manner as described above.

Next, a fourth embodiment of the present invention will be described. The configuration of an image display device according to the fourth embodiment is the same as the configuration of the image display device according to the first embodiment shown in FIG. 2, and only the processing performed by the common region determination unit 22 is different. Accordingly, the detailed description of the device will be omitted herein. The fourth embodiment is different from the first embodiment in that at least a partial region of the subject region included in each of a plurality of three-dimensional images is extracted and a common region is determined by performing registration of at least the extracted partial region of the subject region between tomographic images. The subject region is a region where the subject that is an imaging target in the tomographic image is present.

Figure 14:
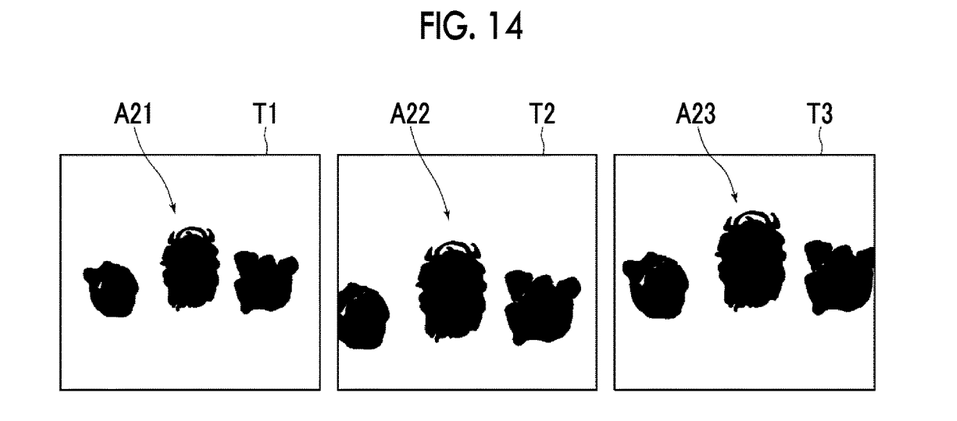
FIG. 14 is a diagram showing a tomographic image on which binarization processing has been performed in a fourth embodiment.

In the fourth embodiment, the common region determination unit 22 extracts at least a partial region of the subject region included in the tomographic image. In the present embodiment, it is assumed that the entire region of the subject region is extracted. Specifically, it is possible to use a method of extracting a subject region by performing histogram analysis of a tomographic image, a method of extracting a subject region by extracting the outline included in a tomographic image, and the like. The common region determination unit 22 divides a tomographic image into a subject region and the other region by performing binarization processing on the tomographic image. FIG. 14 is a diagram showing a tomographic image subjected to binarization processing. FIG. 14 shows a result obtained by extracting a subject region from each of the tomographic images T1 to T3 in the first embodiment and performing binarization processing. As shown in FIG. 14, in the tomographic images T1 to T3, subject regions A21, A22, and A23 are separated from the other background region.

The common region determination unit 22 performs registration of the subject regions A21, A22, and A23 by performing parallel movement, rotation movement, and enlargement and reduction of the binarized subject regions A21, A22, and A23. The common region determination unit 22 determines upper, lower, left, and right edge portions closest to the subject regions registered in the tomographic images T1 to T3 based on the result of registration. Since the determination of the upper, lower, left, and right closest edge portions is the same as that in the first embodiment described above, the detailed description thereof will be omitted herein. In the fourth embodiment, instead of the feature points, with a pixel position on the uppermost side, a pixel position on the lowermost side, a pixel position on the leftmost side, and a pixel position on the rightmost side in the subject regions A21, A22, and A23 of the tomographic images T1 to T3 as references, the closest upper edge portion, the closest lower edge portion, the closest left edge portion, and the closest right edge portion are determined. The common region determination unit 22 determines temporary upper, lower, left, and right edge portions as in the first embodiment, and determines a common region.

In the fourth embodiment described above, only a partial region of the subject region in the tomographic image may be extracted to set a common region. For example, only the region of the cervical spine in each of the tomographic images T1 to T3 may be extracted to set a common region including only the region of the cervical spine.

In the fourth embodiment described above, registration may be performed using the extracted subject region without performing binarization processing.

Figure 15:
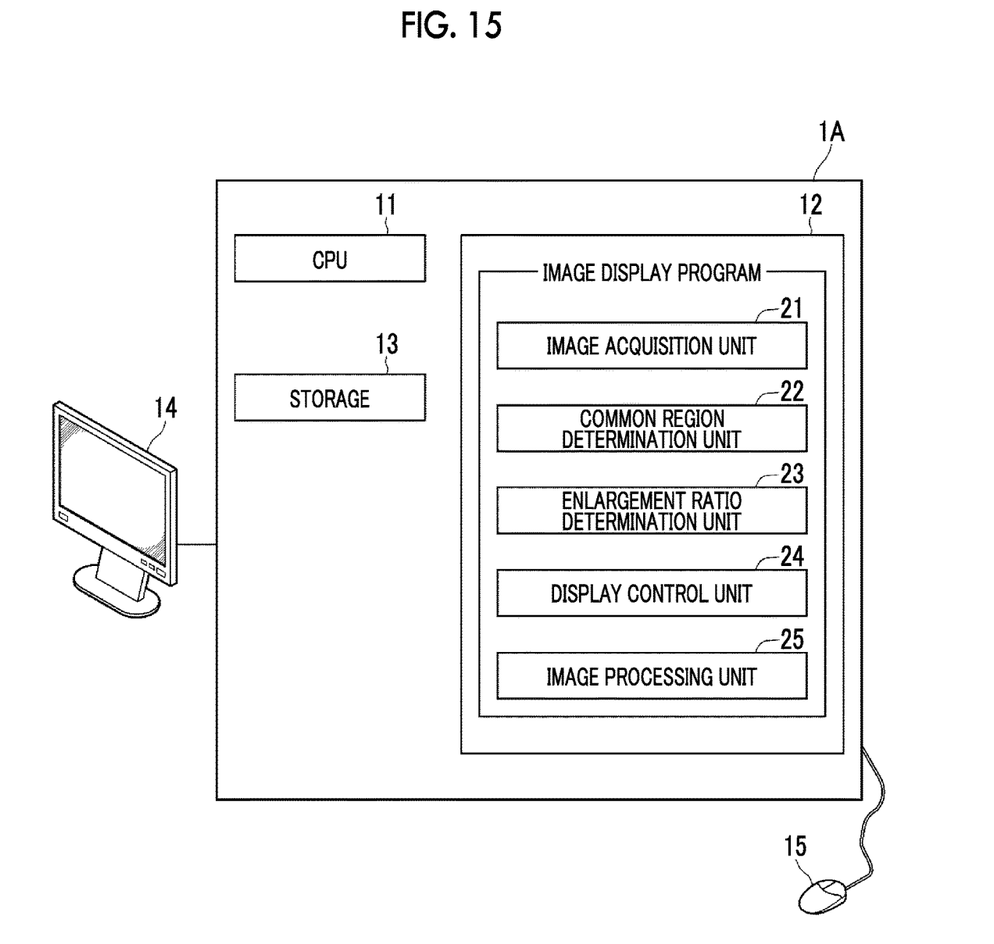
FIG. 15 is a schematic block diagram showing the configuration of an image display device according to a fifth embodiment.

Next, a fifth embodiment of the present invention will be described. FIG. 15 is a schematic block diagram showing the configuration of an image display device according to the fifth embodiment of the present invention. In FIG. 15, the same components as in FIG. 1 are denoted by the same reference numbers, and the detailed description thereof will be omitted. An image display device 1A according to the fifth embodiment is different from the first embodiment in that an image processing unit 25, which performs image processing for matching the image quality on the image of the common region, is provided.

Specifically, the image processing unit 25 performs image processing for matching the density, contrast, and the like of the image of the common region on at least one of a plurality of common regions. For the density, an average density of images of a plurality of common regions may be calculated, and the densities of images of other common regions may be changed so as to match the average density of an image of one of the common regions. For the contrast, a difference value between the maximum density and the minimum density may be calculated for each of the images of the plurality of common regions, and the contrast may be changed to change the difference value of images of other common regions so as to match the difference value of an image of one of the common regions.

As described above, by matching the qualities of the images of the common regions, it becomes easy to view the images of the common regions. As a result, it is possible to perform diagnosis more easily.

In each of the embodiments described above, the common region may be determined after matching the actual sizes of the tomographic images with each other. In particular, in a case where pixel spacing information of each tomographic image, that is, information of the distance between the centers of adjacent pixels is given to the three-dimensional image, it is preferable to match the actual sizes of the tomographic images with each other using the pixel spacing information. For example, in the second embodiment, in a case where the pixel spacing information of the tomographic image T11 is 1 mm and the pixel spacing information of the tomographic image T12 is 2 min, the actual sizes of the tomographic image T11 and the tomographic image T12 can be matched with each other by reducing the vertical and horizontal sizes of the tomographic image T12 to ½. By matching the actual sizes of the tomographic images in this manner, it is possible to efficiently determine the common region.

In each of the embodiments described above, the images of the common regions for a plurality of tomographic images are displayed side by side. However, the images of a plurality of common regions may be switched and displayed. In this case, the image of the common region may be switched according to an instruction from the input unit 15, or the image of the common region may be automatically switched every time a fixed time passes. Alternatively, side-by-side display and switching display of the images of a plurality of common regions may be made to be switchable.

In each of the embodiments described above, a display target is a tomographic image. However, the present invention is not limited thereto, and can also be applied to a case where medical images acquired by an ultrasound diagnostic apparatus, an MRI apparatus, a PET apparatus, an X-ray imaging apparatus, and the like are display targets.

In each of the embodiments described above, all the medical images to be examined in comparative interpretation are displayed. However, only a plurality of medical images selected from all the medical images to be examined in comparative interpretation may be displayed. In this case, determination of the common region, determination of the enlargement ratio, and display of the image of the common region may be performed only for the plurality of selected medical images. For example, in the first embodiment described above, in a case where the tomographic images T1 and T2 are selected from the tomographic images T1 to T3, determination of the common region, determination of the enlargement ratio, and display of the image of the common region may be performed only for the tomographic images T1 and T2. Alternatively, determination of the common region and determination of the enlargement ratio may be performed for all the medical images, and display of the image of the common region may be performed only for the plurality of selected medical images.

Hereinafter, the effect of the present embodiment will be described.

By extracting feature points from a plurality of medical images and determining common regions by matching the feature points among the plurality of medical images, it is possible to efficiently determine the common regions.

By extracting anatomical regions common to a plurality of medical images from a plurality of medical images and determining common regions based on the extracted anatomical regions, it is possible to efficiently determine the common regions.

In a case where a plurality of anatomical regions are present in each of the plurality of medical images, one anatomical region is extracted from each of the plurality of medical images. Based on the positional relationship between one anatomical region extracted in one of the plurality of medical images and other anatomical regions other than the one anatomical region, other anatomical regions in the other medical images other than the one medical image are determined. Based on the one anatomical region and the other anatomical regions extracted in the plurality of medical images, common regions are determined. Therefore, simply by designating a region for one medical image, it is possible to determine the designated region as a common region in each of the plurality of medical images and display the common region on the display unit.

By determining common regions by extracting at least a partial region of the subject region from each of the plurality of medical images and performing registration of at least the partial region of the subject region among the plurality of medical images, it is possible to efficiently determine the common regions.

What is claimed is:

1. An image display device, comprising:
    image acquisition unit for acquiring a plurality of medical images;
    common region determination unit for determining common regions commonly present in the plurality of medical images;
    enlargement ratio determination unit for determining an enlargement ratio, which is for displaying the plurality of common regions in the plurality of medical images with the same size, for each of the plurality of medical images; and
    display control unit for applying the determined enlargement ratio to the plurality of common regions and displaying images of the plurality of common regions after applying the enlargement ratio on display unit,
    wherein the common region determination unit extracts anatomical regions common to the plurality of medical images from the plurality of medical images, and determines the common regions based on the extracted anatomical regions, and
    wherein, in a case where a plurality of anatomical regions are present in each of the plurality of medical images, the common region determination unit extracts one anatomical region from each of the plurality of medical images, determines other anatomical regions in other medical images other than one medical image of the plurality of medical images based on a positional relationship between the one anatomical region extracted in the one medical image and the other anatomical regions other than the one anatomical region, and determines the common regions based on the one anatomical region and the other anatomical regions extracted in the plurality of medical images.

2. The image display device according to claim 1,
    wherein the common region determination unit determines the common regions by matching actual sizes of the plurality of medical images with each other.

3. The image display device according to claim 2,
    wherein the common region determination unit matches the actual sizes with each other based on information of a distance between centers of adjacent pixels, which is given to each of the plurality of medical images.

4. The image display device according to claim 1,
    wherein the display control unit displays images of rectangular regions including the common regions on the display unit.

5. The image display device according to claim 1,
    wherein the display control unit displays images of the plurality of common regions after applying the enlargement ratio side by side.

6. The image display device according to claim 1,
    wherein the display control unit performs switching display among images of the plurality of common regions after applying the enlargement ratio.

7. The image display device according to claim 1, further comprising:
    image processing unit for performing image processing for matching image qualities for images of the plurality of common regions.

8. An image display method, comprising:
    acquiring a plurality of medical images;
    determining common regions commonly present in the plurality of medical images;
    determining an enlargement ratio, which is for displaying the plurality of common regions in the plurality of medical images with the same size, for each of the plurality of medical images; and
    applying the determined enlargement ratio to the plurality of common regions and displaying images of the plurality of common regions after applying the enlargement ratio on display unit,
    wherein anatomical regions common to the plurality of medical images from the plurality of medical images are extracted, and the common regions based on the extracted anatomical regions are determined, and
    wherein, in a case where a plurality of anatomical regions are present in each of the plurality of medical images, one anatomical region from each of the plurality of medical images is extracted, other anatomical regions in other medical images other than one medical image of the plurality of medical images are determined based on a positional relationship between the one anatomical region extracted in the one medical image and the other anatomical regions other than the one anatomical region, and the common regions based on the one anatomical region and the other anatomical regions extracted in the plurality of medical images are determined.

9. A non-transitory computer-readable storage medium that stores an image display program causing a computer to execute:

a step of acquiring a plurality of medical images;

a step of determining common regions commonly present in the plurality of medical images;

a step of determining an enlargement ratio, which is for displaying the plurality of common regions in the plurality of medical images with the same size, for each of the plurality of medical images; and a step of applying the determined enlargement ratio to the plurality of common regions and displaying images of the plurality of common regions after applying the enlargement ratio on display unit, wherein the step of determining common regions includes extracting anatomical regions common to the plurality of medical images from the plurality of medical images, and determining the common regions based on the extracted anatomical regions, and wherein, in a case where a plurality of anatomical regions are present in each of the plurality of medical images, the step of determining common regions includes extracting one anatomical region from each of the plurality of medical images, determining other anatomical regions in other medical images other than one medical image of the plurality of medical images based on a positional relationship between the one anatomical region extracted in the one medical image and the other anatomical regions other than the one anatomical region, and determining the common regions based on the one anatomical region and the other anatomical regions extracted in the plurality of medical images.

* * * * *